United States Patent
Phan et al.

(10) Patent No.: US 11,786,339 B2
(45) Date of Patent: Oct. 17, 2023

(54) SYSTEMS AND METHODS FOR CUSTOMIZING ORAL APPLIANCE APPEARANCE

(71) Applicant: Smylio Inc., Fremont, CA (US)

(72) Inventors: Loc Phan, Santa Clara, CA (US); Renjith Menon, Campbell, CA (US)

(73) Assignee: Smylio Inc., Fremont, CA (US)

(*) Notice: Subject to any disclaimer, the term of this patent is extended or adjusted under 35 U.S.C. 154(b) by 0 days.

(21) Appl. No.: 17/095,726

(22) Filed: Nov. 11, 2020

(65) Prior Publication Data

US 2021/0137641 A1    May 13, 2021

Related U.S. Application Data

(60) Provisional application No. 63/072,938, filed on Aug. 31, 2020, provisional application No. 62/933,977, filed on Nov. 11, 2019.

(51) Int. Cl.
*A61C 7/00* (2006.01)
*G16H 30/20* (2018.01)
(Continued)

(52) U.S. Cl.
CPC .............. *A61C 7/002* (2013.01); *A61C 7/08* (2013.01); *B29C 51/46* (2013.01); *G05B 19/4097* (2013.01); *G06F 3/0488* (2013.01); *G06F 3/04815* (2013.01); *G06F 30/12* (2020.01); *G16H 30/20* (2018.01); *G16H 40/63* (2018.01); *B29L 2031/753* (2013.01); *G05B 2219/49023* (2013.01)

(58) Field of Classification Search
CPC ....... A61C 7/002; A61C 7/08; A61C 2201/00; G16H 30/20; G16H 40/63; G06F 30/12; G06F 3/04815; G06F 3/0488; B29C 51/46; G05B 19/4097; G05B 2219/49023; B29L 2031/753
See application file for complete search history.

(56) References Cited

U.S. PATENT DOCUMENTS

| 5,975,893 A | 11/1999 | Chishti et al. |
|---|---|---|
| 6,390,812 B1 | 5/2002 | Chishti et al. |

(Continued)

FOREIGN PATENT DOCUMENTS

| CN | 107518953 A | 12/2017 |
|---|---|---|
| CN | 108451658 B | 10/2020 |

(Continued)

OTHER PUBLICATIONS

Bodo, K. International Search Report & Written Opinion for PCT/US/2020/023029, dated Aug. 31, 2020.
(Continued)

*Primary Examiner* — Michael Roswell
(74) *Attorney, Agent, or Firm* — MT HUNT LAW; Marcus T. Hunt

(57) ABSTRACT

A graphical user interface ("GUI") is generated on the display, the GUI has a graphical depiction that simulates a translucence level of an oral appliance. The graphical depiction of the translucence level is adjustable based on a user input. A value based on the user selected translucence level is sent to an external device for determination of manufacturing parameters for the oral appliance.

18 Claims, 8 Drawing Sheets

(51) Int. Cl.
*G16H 40/63* (2018.01)
*G06F 30/12* (2020.01)
*A61C 7/08* (2006.01)
*B29C 51/46* (2006.01)
*G05B 19/4097* (2006.01)
*G06F 3/04815* (2022.01)
*G06F 3/0488* (2022.01)
*B29L 31/00* (2006.01)

(56) References Cited

U.S. PATENT DOCUMENTS

| | | | |
|---|---|---|---|
| 6,450,807 | B1 | 9/2002 | Chishti et al. |
| 6,454,565 | B2 | 9/2002 | Phan et al. |
| 7,037,108 | B2 | 5/2006 | Chishti et al. |
| 7,131,830 | B2 | 11/2006 | Kobayashi et al. |
| 7,131,836 | B1 | 11/2006 | Kesling |
| 8,235,713 | B2 | 8/2012 | Phan et al. |
| 9,655,693 | B2 | 5/2017 | Li et al. |
| 9,872,743 | B2 | 1/2018 | Kim |
| 10,549,511 | B2 | 2/2020 | Stewart |
| 11,317,992 | B2 | 5/2022 | Phan |
| 2002/0192617 | A1 | 12/2002 | Phan et al. |
| 2006/0078688 | A1 | 4/2006 | DeSimone et al. |
| 2008/0206715 | A1 | 8/2008 | Kawamoto et al. |
| 2009/0133260 | A1* | 5/2009 | Durbin .............. A61C 13/0004 29/896.11 |
| 2009/0311511 | A1* | 12/2009 | Obuchi ................ B29C 51/002 428/323 |
| 2010/0129763 | A1 | 5/2010 | Kuo |
| 2011/0247214 | A1 | 10/2011 | Huge |
| 2012/0254781 | A1* | 10/2012 | Larsen ................ G06F 3/0481 715/765 |
| 2015/0366637 | A1 | 12/2015 | Kopelman et al. |
| 2016/0092041 | A1* | 3/2016 | Pickens ................ B33Y 50/00 715/771 |
| 2017/0112594 | A1 | 4/2017 | Hilliard |
| 2017/0239017 | A1 | 8/2017 | Kim |
| 2017/0239018 | A1 | 8/2017 | Kim |
| 2018/0235731 | A1 | 8/2018 | Hung |
| 2018/0333226 | A1 | 11/2018 | Tsai et al. |
| 2018/0368961 | A1 | 12/2018 | Shanjani et al. |
| 2019/0105881 | A1 | 4/2019 | Stewart et al. |
| 2019/0239987 | A1* | 8/2019 | Jones ...................... A61C 7/08 |
| 2020/0015937 | A1 | 1/2020 | Stewart |
| 2020/0147856 | A1 | 5/2020 | Culp et al. |
| 2020/0237478 | A1 | 7/2020 | Chang et al. |
| 2021/0078357 | A1 | 3/2021 | Venkatasanthanam et al. |
| 2022/0234779 | A1 | 7/2022 | Spohn et al. |

FOREIGN PATENT DOCUMENTS

| | | |
|---|---|---|
| CN | 106029001 B | 8/2022 |
| EP | 1570803 A2 | 7/2005 |
| EP | 1905380 B1 | 1/2009 |
| JP | 2018134401 A | 8/2018 |
| RU | 2610911 C1 | 2/2017 |

OTHER PUBLICATIONS

Kerner Int.l' Search Report and Written Opinion for PCT/US2020/060066, dated Feb. 23, 2021.

Scheu, Biostar Operating Manual, DE/GB/FR/IT/ES/1.000/06/19 G REF PM 0113.01, downloaded from http://products.scheu-dental.com/documents/5000/1-DOC/0/0/0/0/2/BIOSTAR_SCAN_BA_PM0113_Original_2977.pdf on Apr. 16, 2020.

Scheu, Application booklet for the pressure moulding technique, GB 2.000/07/19 G REF 0111.02, downloaded from https://www.scheu-dental.com/fileadmin/SCHEU-DENTAL/Downloads/06_Sonstiges/BIO_MINI_BRO_0111_GB.pd on Apr. 16, 2020.

Erkodent, Thermoforming, Stzt-EN-03-2020_web, Apr. 2020, downloaded from https://www.erkodent.de/wp-content/documents/products/tzlbrosch_EN.pdf on Apr. 16, 2020.

Erkodent, Erkoform-3D+ Instructions, BA-Erkoform-3d+-anl-EN-Apr. 4, 2019, downloaded from https://www.erkodent.de/wp-content/documents/products/3d+_anl_einzel_EN.pdf on Apr. 16, 2020.

Chadwick et al., "The perception of gloss: A review." Vision Research, vol. 109, Part B, Apr. 2015, pp. 221-235.

Luo et al., "Assessing Gloss of Tooth using Digital Imaging." Conference on Colour in Graphics, Imaging, and Vision, CGIV 2008 Final Program and Proceedings, pp. 307-311.

* cited by examiner

SYSTEMS AND METHODS FOR CUSTOMIZING ORAL APPLIANCE APPEARANCE

CROSS-REFERENCE TO RELATED APPLICATIONS

This application claims the benefit of U.S. Provisional Application No. 62/933,977, filed on Nov. 11, 2019, and U.S. Provisional Application No. 63/072,938, filed on Aug. 31, 2020. Each of the preceding applications is incorporated by reference herein.

BACKGROUND

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and reactive adjustments to the braces by the practitioner, the appliances to move the teeth toward their final destination.

More recently, alternatives to conventional orthodontic treatment with traditional affixed appliances (e.g., braces) have become available. For example, systems including a series of molded plastic aligners have become commercially available from Align Technology, Inc., San Jose, Calif., under the trade name Invisalign® System. The Invisalign® System is described in numerous patents and patent applications assigned to Align Technology, Inc. including, for example in U.S. Pat. Nos. 6,450,807, and 5,975,893. Such aligners are commonly called "clear" aligners due to a transparent plastic construction. Similarly constructed (i.e., thicker) clear retainers (e.g. ESSIX retainers) also exist as a post-procedure option for orthodontic patients.

Clear aligners and retainers are popular among patients over patients for ease of use and aesthetic reasons, as the clear plastic touted as being much less noticeable by others. While clear aligners and retainers may be more aesthetically acceptable to some, such devices are not "invisible." The devices add an unnatural gloss to the teeth due to light interactions with the transparent plastic. For some patients, this gloss effect reduces appliance wear compliance.

SUMMARY OF THE INVENTION

Some embodiments relate to a method for generating determining translucency of an orthodontic appliance.

Some embodiments relate to a method for creating an oral appliance.

Some embodiments relate to a network access device that can have at least one processor.

In some embodiments, a graphical user interface having a graphical depiction that simulates translucence level of an oral appliance can be generated.

In some embodiments, translucence can be adjusted for a graphical depiction of the translucence level can be adjusted based on a user input to a graphical user interface to display a user selected translucence level.

In some embodiments, a user selected translucence level can be transmitted to an external device for determination of manufacturing parameters for the oral appliance.

In some embodiments, a value based on the user selected translucence level can be sent to an external device for manufacturing an oral appliance according to the user selected translucence level.

In some embodiments, a translucency selection value can be received from an external device.

In some embodiments, manufacturing parameters can be determined based on the translucency selection value.

In some embodiments, an oral appliance can be created having an appearance that matches the translucency selection value.

In some embodiments, the manufacturing parameters can include one or more of pressure, vacuum, heat, time, and/or cooling parameters for a thermoforming device.

In some embodiments, a system can include one or more processors configured to execute a method.

In some embodiments, a non-transitory processor-readable medium can include processor-readable instructions that can be configured to cause one or more processors to perform a method.

In some embodiments, a display can be communicatively coupled to at least one processor.

In some embodiments, at least one processor can be configured to cause generation of a graphical user interface on the display.

In some embodiments, a graphical user interface can include a graphical depiction that simulates a translucence level of an oral appliance.

In some embodiments, at least one processor can be configured to adjust the graphical depiction of the translucence level based on a user input.

In some embodiments, a communication interface can be communicatively coupled to the at least one processor.

In some embodiments, at least one processor can be configured to cause a user selected translucence level to be sent via a communication interface to an external device for determination of manufacturing parameters for the oral appliance.

In some embodiments, a display can be a touch screen and a user input can be received via a touch screen.

In some embodiments, a graphical user interface can include a graphical element configured to move according to a user input.

In some embodiments, translucence of a graphical depiction can be adjusted based on where a user positions a graphical element on the touch screen.

In some embodiments, a graphical depiction of the translucence level can be made relatively more opaque or relatively more transparent based on where the user positions the graphical element on a touch screen.

In some embodiments, a graphical depiction can include a 3D model of the patient's oral appliance.

In some embodiments, a 3D model can be rotatable in one or more dimensions.

In some embodiments, a value can be generated by at least one processor according to a relative position of a graphical element that is moved according to a user input to adjust a graphical depiction of a translucence level.

In some embodiments, a value is associated with a range of translucence values obtainable by manipulating thermoforming settings of a thermoforming device used to create an oral appliance.

In some embodiments, an external device can include an appliance manufacturing module.

In some embodiments, an appliance manufacturing module can include a thermoforming device used to create an oral appliance.

BRIEF DESCRIPTION OF THE DRAWINGS

For a better understanding of at least certain embodiments, reference will be made to the following Detailed Description, which is to be read in conjunction with the accompanying drawings.

Figure 1:
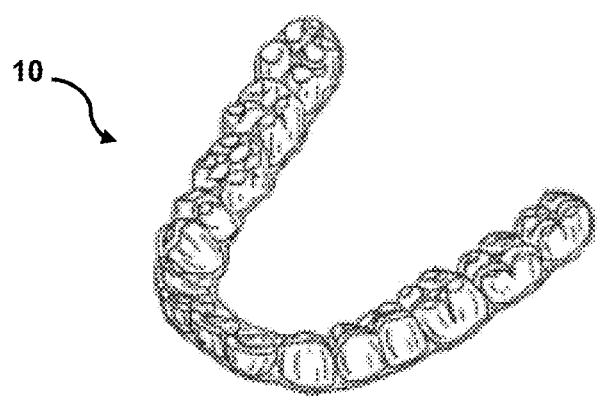
FIG. 1 is a perspective view of an orthodontic appliance, according to some embodiments.

The figures depict various embodiments of the present invention for purposes of illustration only, wherein the figures use like reference numerals to identify like elements. One skilled in the art will readily recognize from the following discussion that alternative embodiments of the structures and methods illustrated in the figures may be employed without departing from the principles of the invention described herein.

DETAILED DESCRIPTION

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order that is logically possible.

FIG. 1 illustrates orthodontic appliance 10, which can be worn by a patient in order to achieve an incremental repositioning of individual teeth or for the purpose of retaining position of moved teeth after completion of an orthodontic treatment (i.e., a "retainer"). In some embodiments, orthodontic appliance 10 can be formed from a laminate of suitable layers of polymeric material. Orthodontic appliance 10 can fit over all teeth present in an upper or lower jaw, or less than all of the teeth.

In some embodiments, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Basic methods for determining an orthodontic treatment plan using a series of incremented appliances as well as instructions for molding orthodontic appliances are well known, and, for example, are described in U.S. Pat. Nos. 6,450,807, and 5,975,893, which are incorporated by reference herein, but only to an extent that those references do not contradict the newer teachings disclosed herein.

An appliance can be designed and/or provided as part of a set of a plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The orthodontic appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The orthodontic appliances are generally not affixed to the teeth and the patient may place and replace the appliances at any time during the procedure (e.g., patient-removable appliances).

Figure 2A:
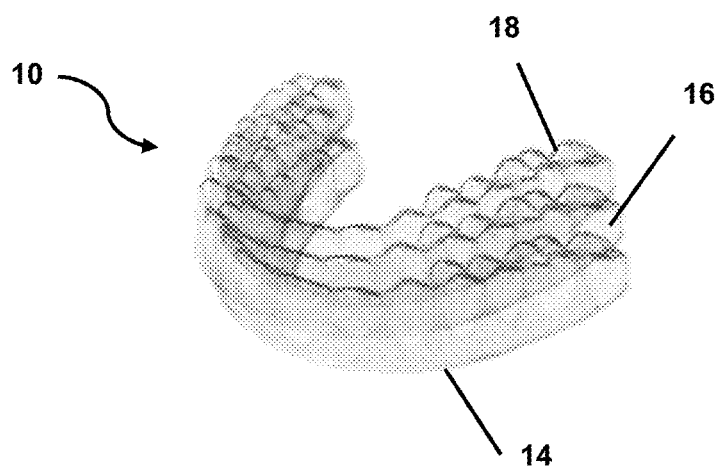
FIGS. 2A is an exploded view of an orthodontic appliance, according to some embodiments.

FIG. 2A shows an exploded view of orthodontic appliance 10. The orthodontic appliance 10 can include a first layer 14 having a teeth engaging surface, a second layer 16 over the first layer and a third layer 18 having an outer surface that is exposed to the oral cavity. In some embodiments, one or more additional layers can be located between the first layer 14 and the second layer 16 and/or between second layer 16 and third layer 18.

In some embodiments, third layer 18 is not included and therefore only first layer 14 and second layer 16 are included, with second layer 16 being the tooth engaging layer.

Figure 2B:
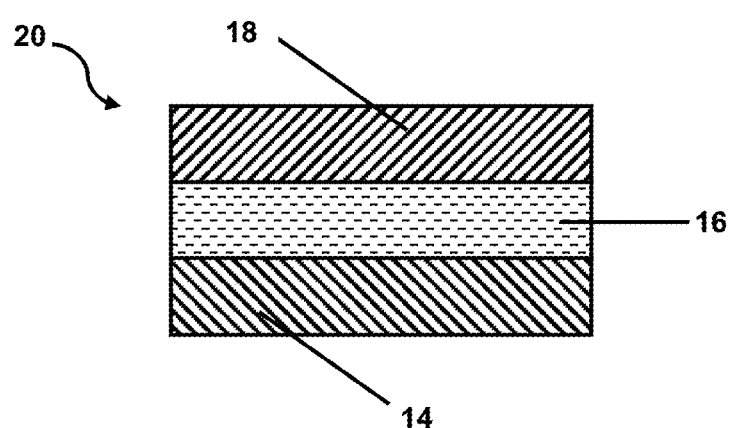
FIG. 2B is a cross-section of a laminate material, according to some embodiments.

While the orthodontic appliance 10 is shown in an exploded view for the purpose of better understanding, the layers of the orthodontic appliance 10 are intended to be of a single sheet of laminate material. A cross-section of laminate material 20 is shown at FIG. 2B. Laminate material 20 can be formed as a co-extruded or co-laminated sheet.

Scientific theory of human perception of gloss is complex and evolving. One study found that six types of perceived gloss, i.e., gloss perceptions, exist: 1. specular gloss (i.e., perceived shininess, perceived brilliance of highlights); 2. Sheen at grazing angles, which is the perceived gloss at grazing angles of otherwise matte surfaces; 3. Contrast gloss, which is identified by contrasts between specularities and the rest of a surface (i.e., observed contrast between specular highlights and otherwise diffusely reflecting surface areas); 4. Haze—this is the presence of a hazy or milky appearance adjacent to reflected highlights (e.g. haze surrounding a reflected highlight on a brushed metal surface); 5. Distinctness-of-reflected-image gloss—(i.e., the perceived distinctness and sharpness of a pseudoimage seen reflected in a surface); and 6. Absence-of-surface-texture gloss—this is the perceived smoothness of a surface, where non-uniformities of surface texture such as blemishes are not visible. See Chadwick et al., "The perception of gloss: A review." *Vision Research*, Vol. 109, Part B, April 2015, Pages 221-235. See also Luo et al., "Assessing Gloss of Tooth using Digital Imaging." *Conference on Colour in Graphics, Imaging, and Vision*, CGIV 2008 Final Program and Proceedings, pp. 307-311. These publications are incorporated by reference. Accordingly, the presence of different types of gloss perceptions (e.g., brilliance next to haziness within a reflected image) on one surface can result in a high perception of gloss.

Accordingly, aspects that contribute to perceived gloss of a prior art clear aligner can include (among others): gloss perceptions derived from light interaction on the outer surface of the clear material; gloss perceptions derived between light interaction between surfaces of the outer and inner surface of the clear material; gloss perceptions derived from light interaction with trapped saliva between the aligner and the tooth surface; perceptions derived from light interaction with air gaps between the aligner and the tooth surface; and gloss perceptions derived from light interaction at inner and outer surface concavity changes (e.g., inner/outer surface lines at gaps between teeth, gumlines). Put another way, a prior art clear aligner suffers from disparate appearances of high specular gloss, image reflections, shiny surfaces, and dark contrast at the creases/lines between teeth and gumline. The thickness of prior art clear appliances (typically 0.030-0.045 inches (0.75-1.00 mm)) contributes to these issues by increasing reflective distortion.

Light transmittance is the ratio of light intensity passing through a material to the intensity of light received by the specimen. Transmittance is determined by light reflection, absorption, and scattering at the material. A highly transparent material has very little absorptive and scattering properties. An opaque material transmits little to no light because of high scattering and absorptive qualities. Translucent materials have relatively high transmittance ratios, because of negligible absorption, but greatly scatter the transmitted light, resulting in a hazy, white appearance. First layer 14 and third layer 18 can be transparent and second layer 16 can be a translucent material or an opaque or nearly opaque material. The result can be very visually similar (as perceived by the human eye) to the appearance of natural teeth while mitigating gloss perceptions of prior art clear appliances.

Some embodiments of the invention include one or more transparent layers laminated over a translucent layer or an opaque layer. Embodiments of the invention reduce perceived glossiness by: including a thinner transparent layer(s) to reduce reflective gloss perceptions derived from light interaction between internal transparent surfaces; including a thinner transparent layer to reduce gloss perceptions derived from light interaction at inner and outer surface concavity changes; including a laminated internal translucent or opaque layer to eliminate gloss perceptions derived from reflections of teeth surfaces; including a laminated internal translucent layer to eliminate gloss perceptions derived from air gaps between the transparent layer and the translucent or opaque layer; including a laminated translucent layer to eliminate gloss perceptions derived from light interaction with trapped saliva; and including a thinner transparent layer(s) to reduce gloss perceptions derived from light interaction at surface changes (i.e., hard surface lines at gaps between teeth, gumlines).

In some embodiments, one or more of first layer 14, second layer 16, and third layer 18 can have thicknesses ranging from 0.001-0.040 inches (0.025-1.02 mm) thick. In some embodiments, the total thickness of laminate material 20 can range from 0.020-0.050 inches (0.51-1.27 mm). In some embodiments, first layer 14, second layer 16, and/or third layer 18 are 0.015 inches thick prior to forming (e.g. thermoforming) laminate material 20 into appliance 10. In some embodiments, first layer 14, second layer 16, and/or third layer 18 are 0.010 inches thick prior to forming (e.g. thermoforming) laminate material 20 into appliance 10.

In some embodiments, first layer 14, second layer 16, and third layer 18 can be constructed from one or polymers such as a polyester, a copolyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof.

In some embodiments, first layer 14 and/or third layer 18 are each formed from a transparent polymer having low haze, high gloss, high transparency, high regular transmittance, and high total transmittance. For example, for a 0.010 inch (0.25 mm) sample light transmission values can include 0.5-1.5% Haze (ASTM D1003), >80 GU@45° (ASTM D2457), >80% transparency (ASTM D1746), >80% regular transmittance (ASTM D1003 modified), and/or >80% total transmittance (ASTM D1003 Modified)). In some embodiments, a transparent copolyester (e.g., Eastar™ copolyester 6763) can be used having the following properties: (for a 0.010 inch (0.25 mm) sample: 0.8% Haze (ASTM D1003), 108 GU@45° (ASTM D2457), 85% Transparency (ASTM D1746), 89% Regular Transmittance (ASTM D1003 Modified), 91% Total Transmittance (ASTM D1003 Modified)).

In some embodiments, first layer 14 and third layer 18 are each transparent and formed from one or more polymers. In some embodiments, to provide a long service life when oral appliance 10 is a retainer, first layer 14 and/or third layer 18 are selected from materials having high impact resistance. In some embodiments, first layer 14 and third layer 18 are made primarily or entirely from polyethylene terephthalate glycol-modified (PETG). In some embodiments, first layer 14 and/or third layer 18 are made primarily or entirely from polycarbonate. In some embodiments, first layer 14 and/or third layer 18 are made primarily or entirely from polymethylmethacrylate (PMMA).

In some embodiments, first layer 14 and/or third layer 18 is processed to reduce or remove hydrophobic properties (e.g., from PETG) that can induce saliva foaming. In some embodiments, first layer 14 and/or third layer 18 is processed (e.g. rolled) to have a matte outer surface finish to reduce or remove hydrophobic properties. In some embodiments, first layer 14 and/or third layer 18 is processed with an acid or a base to reduce or remove hydrophobic properties. In some embodiments, first layer 14 and/or third layer 18 are covered with coatings or additional layers having hydrophilic properties.

In some embodiments, second layer 16 is formed from one or more translucent polymers, which can provide a hazed white appearance. In some embodiments, second layer 16 is primarily or entirely made of polyurethane, thermoplastic elastomer such as a thermoplastic copolyester (TPC/TPE-E) (e.g. Arnitel® EM400/EM460), maleic anhydride grafted polyethylene (HDPE) (e.g. Westlake Plastics® GB1002), or reactive terpolymer (e.g. Lotader® blends). In some embodiments, second layer 16 can be processed to increase crystallinity, thereby increasing light scattering to reduce transparency, increase translucence and provide a white or milky appearance. In some embodiments, second layer 16 has greater flexibility (e.g., at least 1.5× less flexural modulus) than first layer 14 and/or third layer 18 to provide oral appliance 10 with greater flexibility.

In some embodiments, second layer 16 can be an opaque or nearly opaque material, such as a polymer having a white colorant (e.g. titanium dioxide particles) or a metal foil. In some embodiments, a metal foil can be coated with titanium dioxide to provide a white appearance.

Figure 3:
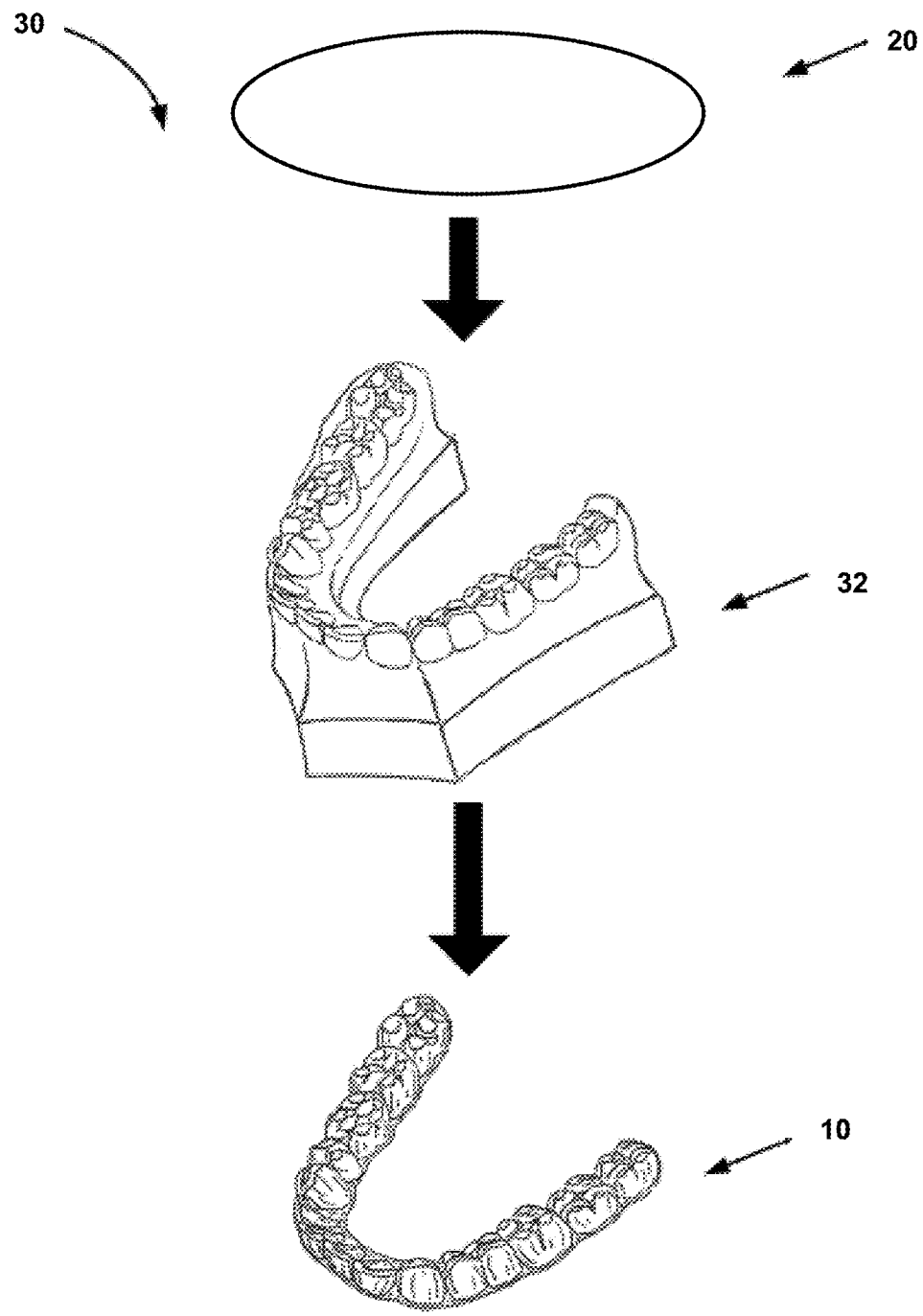
FIG. 3 is a perspective view of a process for molding an orthodontic appliance, according to some embodiments.

FIG. 3 depicts an example of process 30 for forming an orthodontic appliance. As shown, laminate material 20 can be formed into orthodontic appliance 10. In this example process, orthodontic appliance 10 can be produced with the use of physical tooth model, or mold, 32. In some embodiments, laminate material 20 is dimensioned (e.g., 120 mm and/or 125 mm diameter circle) for ready processing on a commercially available forming device (e.g., Erkoform®, Erkoform-3dmotion®, Biostar®, Ministar S®, Drufomat Scan®, Drufosmart®, Essix® SelectVac®). Guidelines for operating such forming devices can be found at Scheu Dental Technology, *Biostar Operating Manual*, DE/GB/FR/IT/ES/1.000/06/19 G REF PM 0113.01; Scheu Dental Technology, *Application booklet for the pressure moulding technique*, GB 2.000/07/19 G REF 0111.02; Erkodent, *Thermoforming*, S15-3106-48; Erkodent, *Erkoform 3D*, 61-8002-2; Erkodent, *Erkoform-3D+Instructions*, BA-Erkoform-3d+-anl-EN-04-04-2019, which are incorporated by reference herein.

Orthodontic appliance 10 can be produced by heating laminate material 20 and then vacuum or pressure forming the material over the teeth in the physical tooth model 32, and then trimming excess material after removal from the mold. Accordingly, orthodontic appliance 10 is a direct representation of physical tooth model 32.

In some embodiments, second layer 16 of laminate material 20 (e.g. thermoplastic copolyester (TPC/TPE-E) (e.g. Arnitel® EM400/460)) is provided in a crystalized form, such that it appears translucent or opaque prior to thermoforming. Some thermoplastic elastomers allow one to tune the amount of translucency according to the heating temperature and/or heating time. Thermoforming laminate material 20 for a sufficient amount of time can modify (i.e., decrystalize) the crystalline structure of second layer 16 to make it translucent, or at least more translucent than originally provided. The degree of translucence depends on the amount of time laminate material 20 is thermoformed and/or the temperature applied (i.e. thermoforming machine temperature setting) to laminate material, the thickness of second layer 16, and the thickness of first layer 14 and third layer 18.

It has been determined that heating times of 30-60 seconds using a Biostar thermoforming device (with thermoforming settings 6 bar/87 psi, 427° F.) on laminates with first layer 14 and third layer 18 ranging from 0.010-0.015 in. thick and second layer 16 being 0.010 in. thick provided a good translucency for orthodontic retainers resembling human teeth. The ability to tune translucence (for oral appliances using at least one thermoplastic elastomer layer) can be advantageous over appliances that use colorants such as TiO2 or BaSO4 or using materials such as crystallized polyethylene and polypropylene, which, for the purposes of thermoforming an appliance, the degree of possible translucency or opaqueness are more or less set when such materials are formed.

In some embodiments, an oral appliance can be constructed from a laminate shaped to fit in a commercially available thermoforming device and has an optimal thickness of 0.020-0.045 inches (prior to thermoforming). In some embodiments, first layer 14 and third layer 18 can each be formed from a transparent copolyester (e.g., PETG such as Eastar™ copolyester 6763) having an optimal thickness of 0.005-0.020 inches (prior to thermoforming), and a second layer 16 being formed from a thermoplastic elastomer (e.g. TPC/TPE-E such as Arnitel® EM400) having an optimal thickness of 0.005-0.020 inches (prior to thermoforming).

Figure 4A:
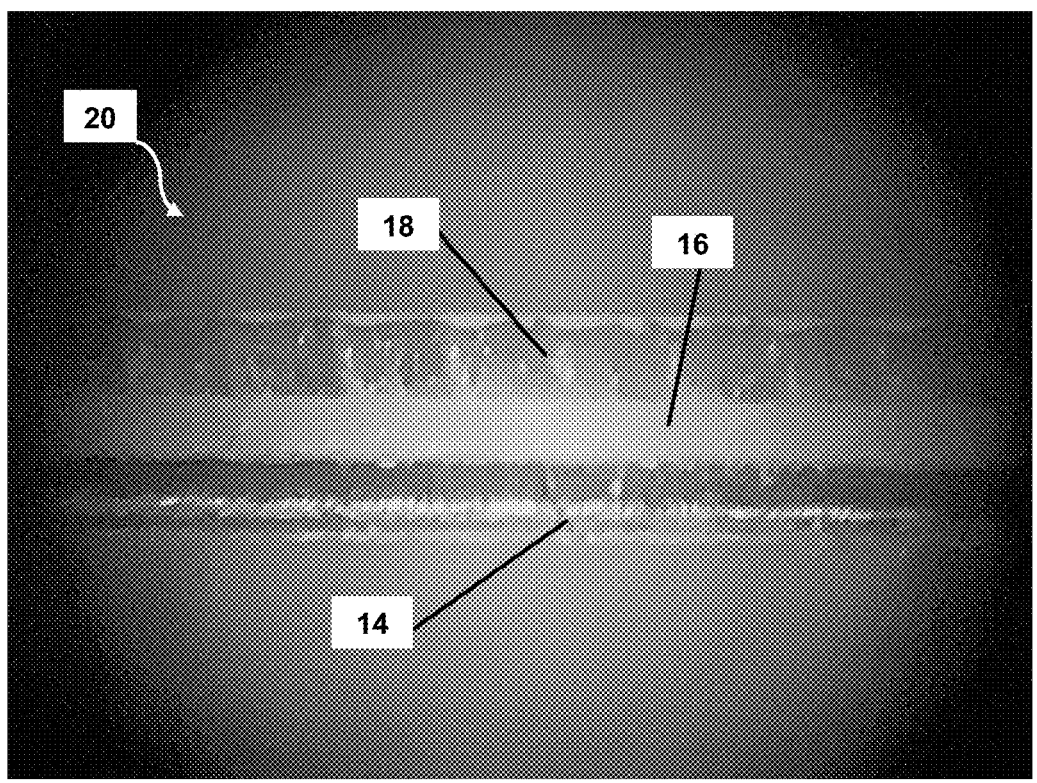
FIG. 4A is a photograph of a cross-section of a laminate material, according to some embodiments.
Figure 4B:
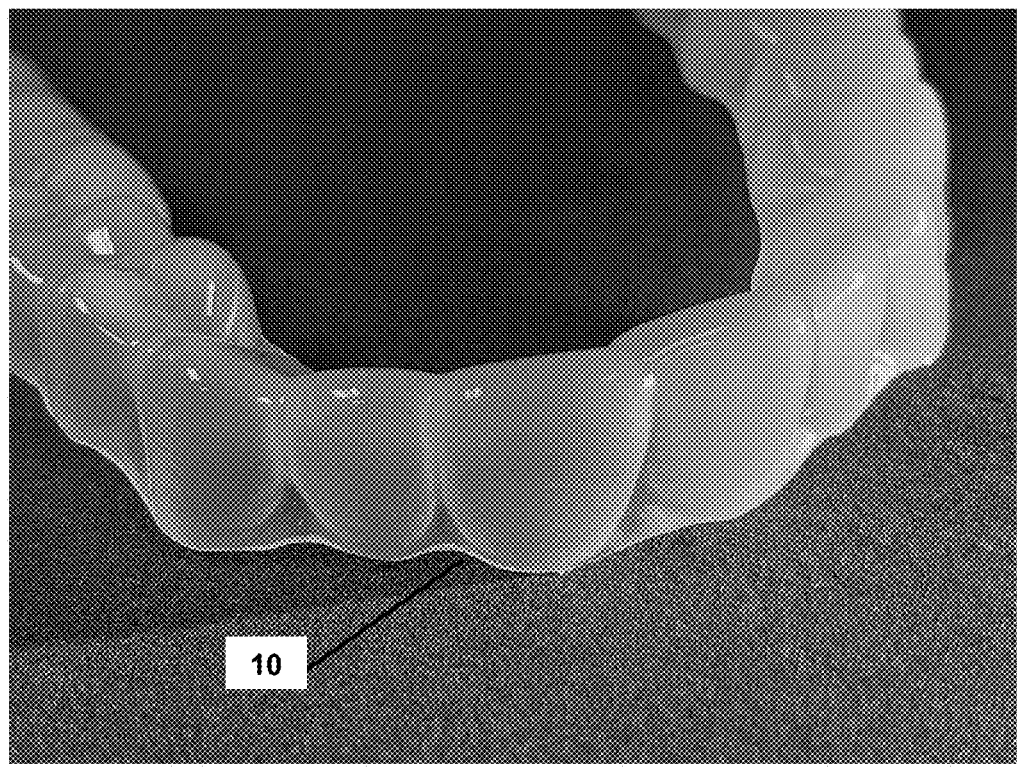
FIG. 4B is a photograph of the laminate material of FIG. 4A formed into an orthodontic appliance, according to some embodiments.

As shown in FIGS. 4A and 4B, in some embodiments, laminate material 20 can be thermoformed into a retainer 10 having an optimal thickness of 0.040 inches (prior to thermoforming), where first layer 14 and third layer 18 can each be formed from a transparent copolyester (e.g., PETG such as Eastar™ 6763) having an optimal thickness of 0.015 inches (prior to thermoforming), and a second layer 16 being formed from a thermoplastic copolyester (TPC/TPE-E) (e.g. Arnitel® EM400) having an optimal thickness of 0.010 inches (prior to thermoforming). As shown in the photograph of a cross-section of laminate material 20 at FIG. 4A, second layer 16 is opaque prior to thermoforming. Compare with retainer 10 of FIG. 4B, in which heating laminate material 20 during a thermoforming process causes second layer 16 to decrystallize to a degree from an opaque state to become translucent or have relatively greater transparency.

As described above, the degree of crystallinity can be tuned to increase or decrease relative translucency of second layer 16 and hence retainer 10. It has been determined that using laminate material 20 with a commercially available Biostar® thermoforming device with a heating setting of 220° C./427° F., heating time of 45-50 seconds, and cooling time of 100-140 seconds or 120 seconds provides the level of translucency (or closely similar) of retainer 10 shown at FIG. 4B. Increasing the heating time will provide greater transparency for retainer 10 via greater relative decrystallization of second layer 16, and conversely decreasing the heating time will provide less transparency for retainer 10 via less relative decrystallization of second layer 16. In some embodiments, the laminate can be thermoformed into an aligner having an optimal thickness of 0.030 inches (prior to thermoforming), where first layer 14 and third layer can each being formed from a transparent copolyester (e.g., Eastar™ copolyester 6763) having an optimal thickness of 0.010 inches (prior to thermoforming), and a second layer 16 being formed from a thermoplastic copolyester (e.g. Arnitel® EM400) having an optimal thickness of 0.010 inches (prior to thermoforming).

Figure 5:
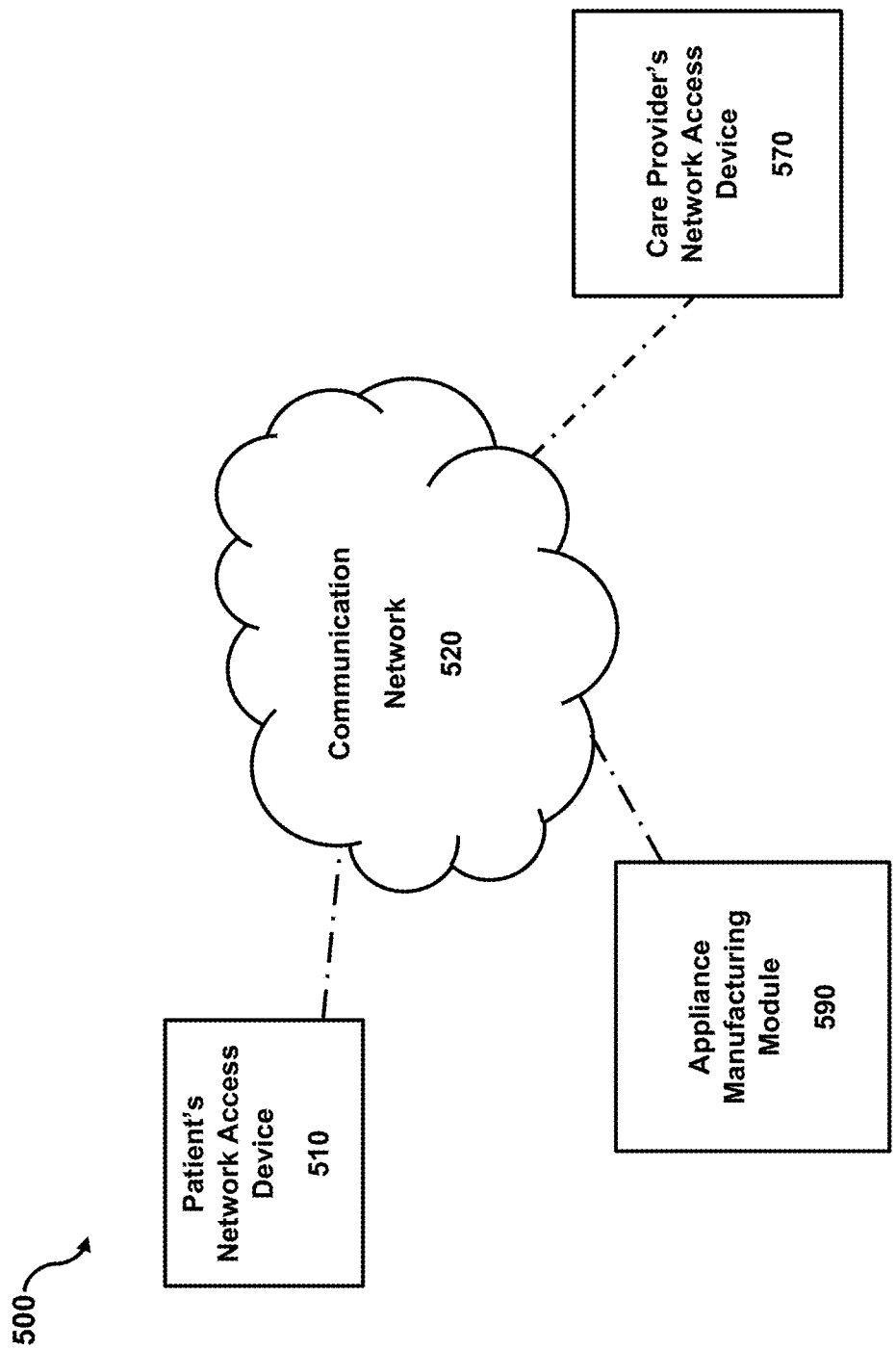
FIG. 5 is a schematic drawing of a network, according to some embodiments.

FIG. 5 illustrates an embodiment of network 500 for facilitating communication with a patient's (or patient accessible) network access device 510. The network access device 510 can be a smart phone, tablet, or a general purpose computer that is configured to communicate via a communication network 520 (e.g., the Internet). The network access device 510 can include a camera that is configured, via an application stored as processor executable instructions on a non-transitory medium readable by a processor of the network access device 510, to record one or more pictures of the patient's teeth and upload the pictures to an image analysis device 530. In some embodiments, the application can also be a platform for private electronic communications (e.g., encrypted text, email, voice, videoconferencing) with a health care provider using network access device 570, for the purpose of evaluating the patient's progress with an orthodontic treatment plan.

In some embodiments, the network access device 510 can be configured by a software application to enable a patient to select a relative degree of translucency for a one or more particular oral appliances. In some embodiments, the software application can include a graphical user interface ("GUI") that provides a variable image of an oral appliance having a user-selectable degree of translucency. In some embodiments, the user can save and send the translucency selection to another aspect of the network so that an oral appliance can be produced according to the translucency selection. In some embodiments, the translucency selection can be a numerical value based on a translucency scale (e.g., 1-100).

Figure 7:
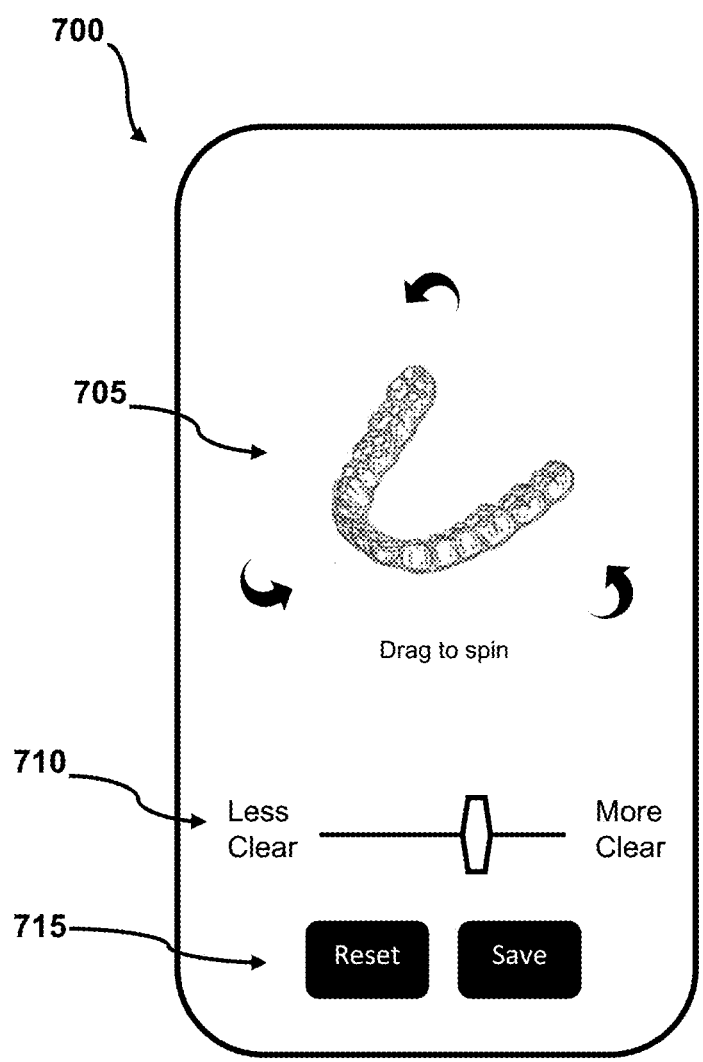
FIG. 7 is a depiction of a GUI, according to some embodiments.

An example of a GUI 700 is shown at FIG. 7, which depicts a screenshot of GUI 700, which, in some embodiments, can be generated by an application stored as processor executable instructions on a non-transitory medium readable by a processor of network access device 510 or a different device (e.g., cloud based server) that interfaces with network access device. In some embodiments GUI 700 can be generated by a software application that includes additional features, for example, such as features described at Int'l. App. No. PCT/US20/45650, which is incorporated by reference herein. In some embodiments, GUI 700 can include a depiction 705 of an orthodontic appliance, which in some embodiments can be of a 3D model of the patient's orthodontic appliance. In some embodiments, the depiction 705 can be made to rotate in 3 dimensions, for example, by way of a user input to a keyboard, mouse, or touch screen interface. In some embodiments, the depiction 705 can be one or more photorealistic renderings of an orthodontic appliance being worn by the patient or a generic human face.

In some embodiments, GUI 700 includes can be configured to receive user input, to affect translucence level of the depiction 705, from an input device, for example, a keyboard or mouse, or a touch screen interface as depicted here. In some embodiments, a touch screen interface is configured as a slidable bar 710, which has an element that can be dragged in one or more directions to affect translucence level (e.g., more clear, less clear) of the depiction 705. In some embodiments, as the slidable bar 710 is moved to the left, the GUI 700 can live render the depiction 705 to become less clear, i.e., more opaque. In some embodiments, as the slidable bar 710 is moved to the right, the GUI 700 can live render the depiction 705 to become more clear, i.e., more transparent. The relative position of the slideable bar 710 can generally be associated with a particular level of relative translucence, which can be a particular value of a range of translucence values obtainable by manipulating thermoforming settings of a thermoforming device as disclosed herein, for example, by thermoforming the laminate material 20.

In some embodiments, GUI 700 includes can be configured to receive user input, to reset or save the selected translucence level, from an input device, for example, a keyboard or mouse, or a touch screen buttons 715 as depicted here. The saved translucence level can be stored on a memory module of the user input device 510 and/or transmitted to a different device via network 520 and/or saved on a database that is associated with the patent's appliance generation records.

In some embodiments, the patient's network access device 510 can provide the translucency selection via the communication network 520 to the care provider's network access device 570, which can in turn incorporate the translucency selection into a design for producing one or more oral appliances. In some embodiments, the design can include a 3D model of an oral appliance, where the 3D model is based images of the patient's teeth. The design can be provided by the care provider's network access device 570 via network 520 to an appliance manufacturing module ("AAM") 590. AAM 590, or a manufacturing aspect in communication with AAM 590, can then process the 3D model of the appliance to create a mold or other manufacturing implement required to create the appliance.

In some embodiments, AAM 590 can be configured, via an application stored as processor executable instructions on a non-transitory medium readable by a processor of the AAM 590. In some embodiments, AAM 590 can include software and/or hardware aspects of a server, special-purpose computer, or general-purpose computer, and communicatively coupled to manufacturing aspects, such as modules for controlling an aligner manufacturing apparatus. In some embodiments, the orthodontic appliance is manufactured according to the process detailed with respect to FIGS. 3, 4A, and 4B.

In some embodiments, AAM 590 can determine manufacturing parameters for thermoforming an orthodontic appliance to conform with the translucency selection of the patient. In some embodiments, the translucency selection can be a numerical value that can be matched by AAM 590 to a scale of values within a look-up table stored on a database, which can include one or more manufacturing parameters that match each value. Such manufacturing parameters can include pressure, vacuum, heat, time, and/or cooling parameters that are applicable to a certain type of thermoforming device. After matching the patient's translucency selection to a particular one or more manufacturing parameters for thermoforming a sheet of material into the orthodontic appliance, AAM 590 can retrieve the associated manufacturing parameters and use them to program a manufacturing apparatus.

Figure 6A:
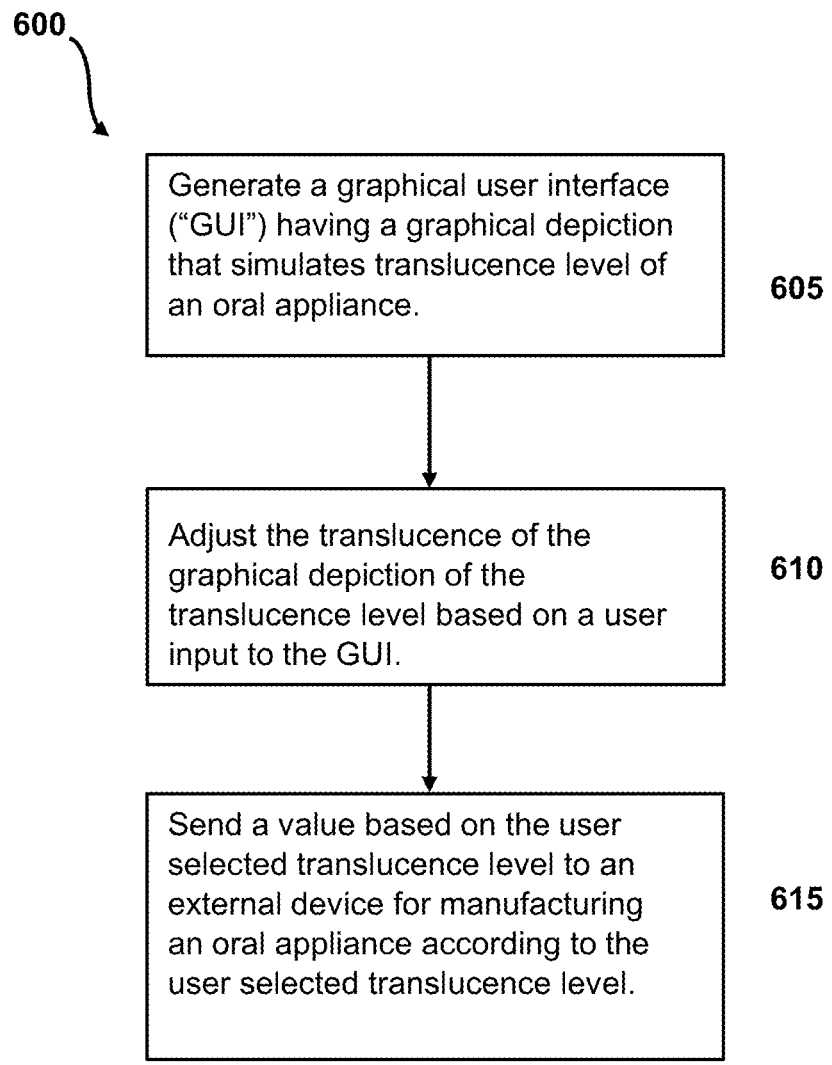
FIGS. 6A and 6B are flow charts of methods, according to some embodiments.

FIG. 6A illustrates method 600 that can be performed by system for generating an oral appliance, such as the system shown at FIG. 5. In some embodiments, all or portions of method 600 can be stored as processor executable instructions on a non-transitory medium readable by one or more processors. The one or more processors can be configured to execute method 600.

At operation 605, the one or more processors can generate a graphical user interface ("GUI") having a graphical depiction that simulates translucence level of an oral appliance. The GUI can include the aspects described with respect to FIG. 7 and generated using network access device 510. The GUI can be configured to receive user input, to affect translucence level of the depiction, from an input device, for example, a keyboard or mouse, or a touch screen interface as depicted here. In some embodiments, a touch screen interface is configured as a slidable bar, which has an element that can be dragged in one or more directions to affect translucence level (e.g., more clear, less clear) of the depiction.

At operation 610, the one or more processors can adjust the translucence of the graphical depiction of the translucence level based on a user input to the GUI. In some embodiments, as the slidable bar is moved on one direction, the GUI can live render the depiction to become less clear, i.e., more opaque. In some embodiments, as the slidable bar is moved to a different direction, the GUI can live render the depiction to become more clear, i.e., more transparent. The relative position of the slideable bar can generally be associated with a particular level of relative translucence, which can be a particular value of a range of translucence values obtainable by manipulating thermoforming settings of a thermoforming device as disclosed herein, for example, by thermoforming the laminate material 20.

At operation 615, the one or more processors can send a user saved value based on the user selected translucence level to an external device for manufacturing an oral appliance according to the user selected translucence level. The GUI can be configured to receive user input, to reset or save the selected translucence level, from an input device, for example, a keyboard or mouse, or a touch screen buttons. The saved translucence level can be stored on a memory module communicatively coupled to the one or more processors and/or transmitted to a different device via a network and/or saved on a database that is associated with the patent's appliance generation records.

Figure 6B:
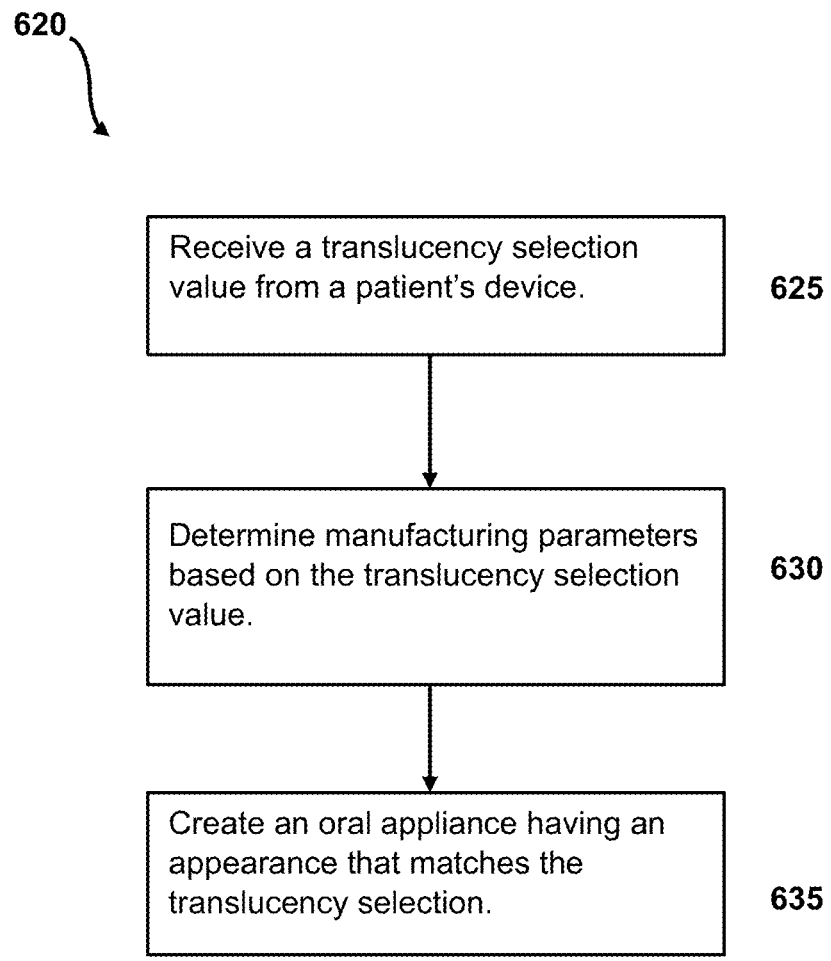

FIG. 6B illustrates method 620 that can be performed by system for generating an oral appliance, such as the system shown at FIG. 5. In some embodiments, all or portions of method 620 can be stored as processor executable instructions on a non-transitory medium readable by one or more processors. The one or more processors can be configured to execute method 620.

At operation 625, the one or more processors can receive a translucency selection from a patient's device. The translucency selection into a design for producing one or more oral appliances. In some embodiments, the design can include a 3D model of an oral appliance, where the 3D model is based images of the patient's teeth. The one or more processors can process the 3D model of the appliance to create a mold or other manufacturing implement required to create the appliance.

At operation 630, the one or more processors can determine manufacturing parameters based on the translucency selection. In some embodiments, the translucency selection can be a numerical value that can be matched by the one or more processors to a scale of values within a look-up table stored on a database, which can include one or more manufacturing parameters that match each value. Such manufacturing parameters can include pressure, vacuum, heat, time, and/or cooling parameters that are applicable to a certain type of thermoforming device.

At operation 635, after matching the patient's translucency selection to a particular one or more manufacturing parameters for thermoforming a sheet of material into the orthodontic appliance, the one or more processors can retrieve the associated manufacturing parameters and use them to program a manufacturing apparatus. Such an apparatus can include all or some of the aspects of the systems depicted at FIGS. 3 and 5.

Figure 8:
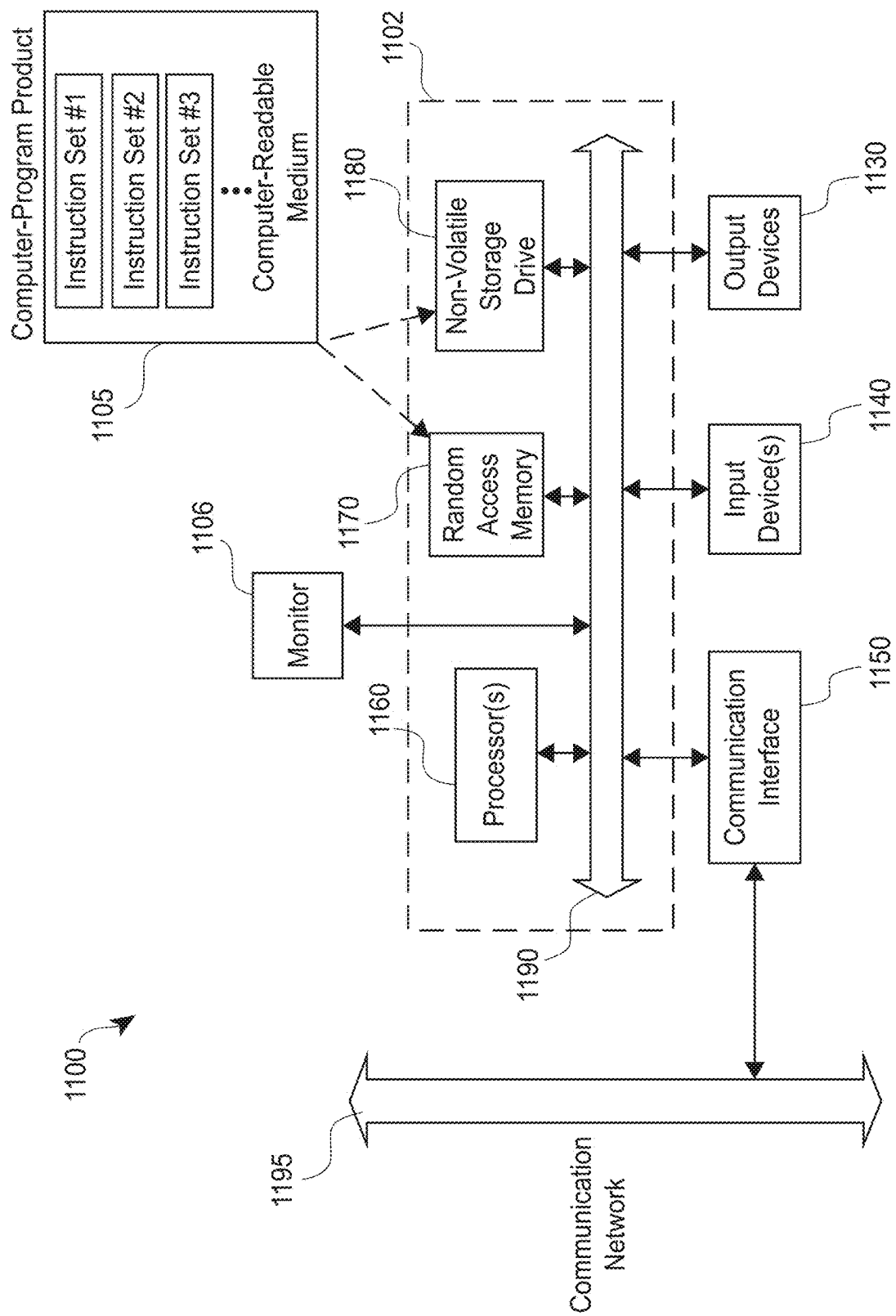
FIG. 8 is a schematic drawing of a computer system, according to some embodiments.

With reference to FIG. 8, an embodiment of a special-purpose computer system 1100 is shown. For example, one or more intelligent components, processing system 110 and components thereof may be a special-purpose computer system 1100. Such a special-purpose computer system 1100 may be incorporated as part of any of the other computerized devices discussed herein, such devices shown at FIG. 5. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general-purpose computer system 1126, it can be transformed into the special-purpose computer system 1100.

Special-purpose computer system 1100 comprises a computer 1102, a monitor 1106 coupled to computer 1102, one or more additional user output devices 1130 (optional) coupled to computer 1102, one or more user input devices 1140 (e.g., keyboard, mouse, track ball, touch screen) coupled to computer 1102, an optional communications interface 1150 coupled to computer 1102, a computer-program product 1105 stored in a tangible computer-readable memory in computer 1102. Computer-program product 1105 directs computer system 1100 to perform the above-described methods. Computer 1102 may include one or more processors 1160 that communicate with a number of peripheral devices via a bus subsystem 1190. These peripheral devices may include user output device(s) 1130, user input device(s) 1140, communications interface 1150, and a storage subsystem, such as random-access memory (RAM) 1170 and non-volatile storage drive 1180 (e.g., disk drive, optical drive, solid state drive), which are forms of tangible computer-readable memory.

Computer-program product 1105 may be stored in non-volatile storage drive 1180 or another computer-readable medium accessible to computer 1102 and loaded into random access memory (RAM) 1170. Each processor 1160 may comprise a microprocessor, such as a microprocessor from Intel® or Advanced Micro Devices, Inc.®, or the like. To support computer-program product 1105, the computer 1102 runs an operating system that handles the communications of computer-program product 1105 with the above-noted components, as well as the communications between the above-noted components in support of the computer-program product 1105. Exemplary operating systems include Windows® or the like from Microsoft Corporation, Solaris® from Sun Microsystems, LINUX, UNIX, and the like.

User input devices 1140 include all possible types of devices and mechanisms to input information to computer 1102. These may include a keyboard, a keypad, a mouse, a scanner, a digital drawing pad, a touch screen incorporated into the display, audio input devices such as voice recognition systems, microphones, and other types of input devices. In various embodiments, user input devices 1140 are typically embodied as a computer mouse, a touch screen, camera, wireless remote, drawing tablet, or voice command system. User input devices 1140 can allow a user to select, input, or add objects, icons, text, photos, and the like that appear on the monitor 1106 via a command such as a click of a button or the like. User output devices 1130 include various types of devices to output information from computer 1102. These may include a display (e.g., monitor 1106), printers, non-visual displays such as audio output devices, etc.

Communications interface 1150 provides an interface to other communication networks, such as communication network 1195, and devices and may serve as an interface to receive data from and transmit data to other systems, WANs and/or the Internet. Embodiments of communications interface 1150 typically include an Ethernet card, a modem (telephone, satellite, cable, ISDN), a (asynchronous) digital subscriber line (DSL) unit, a USB interface, a wireless network adapter, and the like. For example, communications interface 1150 may be coupled to a computer network, or the like. In other embodiments, communications interface 1150 may be physically integrated on the motherboard of computer 1102, and/or may be a software program, or the like.

RAM 1170 and non-volatile storage drive 1180 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1170 and non-volatile storage drive 1180 may be configured to store the basic programming and data constructs that provide the functionality of various embodiments of the present invention, as described above.

Software instruction sets that provide the functionality of the present invention may be stored in RAM 1170 and non-volatile storage drive 1180. These instruction sets or code may be executed by the processor(s) 1160. RAM 1170 and non-volatile storage drive 1180 may also provide a repository to store data and data structures used in accordance with the present invention. RAM 1170 and non-volatile storage drive 1180 may include a number of memories including a main random-access memory (RAM) to store instructions and data during program execution and a read-only memory (ROM) in which fixed instructions are stored. RAM 1170 and non-volatile storage drive 1180 may include a file storage subsystem providing persistent (non-volatile) storage of program and/or data files. RAM 1170 and non-volatile storage drive 1180 may also include removable storage systems, such as removable flash memory.

Bus subsystem 1190 provides a mechanism to allow the various components and subsystems of computer 1102 to communicate with each other as intended. Although bus subsystem 1190 is shown schematically as a single bus, alternative embodiments of the bus subsystem may utilize multiple busses or communication paths within the computer 1102.

Throughout the foregoing description, and for the purposes of explanation, numerous specific details are set forth in order to provide a thorough understanding of the described techniques. It will be apparent, however, to one skilled in the art that these techniques can be practiced without some of these specific details. Although various embodiments that incorporate these teachings have been shown and described in detail, those skilled in the art could readily devise many other varied embodiments or mechanisms to incorporate these techniques. Also, embodiments can include various operations as set forth above, fewer operations, or more operations; or operations in an order. Accordingly, the scope and spirit of the invention should be judged in terms of the claims, which follow as well as the legal equivalents thereof.

What is claimed is:

1. A network access device, comprising:
   at least one processor;
   a display communicatively coupled to the at least one processor, wherein the at least one processor is configured to cause generation of a graphical user interface ("GUI") on the display, the GUI having a graphical depiction that simulates a translucence level of an oral appliance, wherein the at least one processor is configured to adjust the graphical depiction of the translucence level based on a user input; and
   a communication interface communicatively coupled to the at least one processor, wherein the at least one processor is configured to cause a user selected translucence level for the oral appliance for manufacture to be sent via the communication interface to an external device for determination of manufacturing parameters for the oral appliance, wherein the user selected translucence level for the oral appliance for manufacture comprises a value representing one of a plurality of user-selectable degrees of translucency;
   wherein the value is generated by the at least one processor according to a relative position of a graphical element that is moved according to the user input to adjust the graphical depiction of the translucence level, and
   wherein the value is associated with a range of translucence values obtainable by manipulating thermoforming settings of a thermoforming device used to create the oral appliance.

2. The network access device of claim 1, wherein the display comprises a touch screen and wherein the user input is received via the touch screen, and wherein the GUI includes a graphical element configured to move according to the user input.

3. The network access device of claim 2, wherein the translucence of the graphical depiction is adjusted based on where the user positions the graphical element on the touch screen.

4. The network access device of claim 3, wherein the graphical depiction of the translucence level relatively more opaque or relatively more transparent based on where the user positions the graphical element on the touch screen.

5. The network access device of claim 1, wherein the graphical depiction comprises a 3D model of a patient's oral appliance.

6. The network access device of claim 5, wherein the 3D model is rotatable in one or more dimensions.

7. The network access device of claim 1, wherein the external device comprises an appliance manufacturing module.

8. The network access device of claim 7, wherein the appliance manufacturing module comprises a thermoforming device used to create the oral appliance.

9. The network access device of claim 1, wherein the user-selectable degrees of translucency enable the user to select a translucency level of the oral appliance for manufacture that differs from a translucency based on an image of teeth of the patient.

10. A method for generating determining translucency of an orthodontic appliance, the method comprising:
    generating, by at least one processor, a graphical user interface ("GUI") for display on a display, the GUI having a graphical depiction that simulates translucence level of an oral appliance;
    adjusting, by the at least one processor, the translucence of the graphical depiction of the translucence level based on a user input to the GUI to display a user selected translucence level; and
    sending, by at least one processor, the user selected translucence level for the oral appliance for manufacture to an external device for determination of manufacturing parameters for the oral appliance, wherein the user selected translucence level for the oral appliance for manufacture comprises a value representing one of a plurality of user selectable degrees of translucency;
    wherein the value is generated by the at least one processor according to a relative position of a graphical element that is moved according to the user input to adjust the graphical depiction of the translucence level, and
    wherein the value is associated with a range of translucence values obtainable by manipulating thermoforming settings of a thermoforming device used to create the oral appliance.

11. The method of claim 10, wherein the display comprises a touch screen and wherein the user input is received via the touch screen, and wherein the GUI includes a graphical element configured to move according to the user input.

12. The method of claim 11, wherein the translucence of the graphical depiction is adjusted based on where the user positions the graphical element on the touch screen.

13. The method of claim 12, wherein the graphical depiction of the translucence level relatively more opaque or relatively more transparent based on where the user positions the graphical element on the touch screen.

14. The method of claim 10, wherein the graphical depiction comprises a 3D model of the patient's oral appliance.

15. The method of claim 14, wherein the 3D model is rotatable in one or more dimensions.

16. The method of claim 11, wherein the external device comprises an appliance manufacturing module.

17. The method of claim 16, wherein the appliance manufacturing module comprises a thermoforming device used to create the oral appliance.

18. The method of claim 10, wherein the user-selectable degrees of translucency enable the user to select a translucency level of the oral appliance for manufacture that differs from a translucency based on an image of teeth of the patient.

* * * * *